(12) United States Patent
Hadad et al.

(10) Patent No.: US 11,197,751 B2
(45) Date of Patent: Dec. 14, 2021

(54) INTRAOCULAR LENS AND METHODS FOR ACCOMMODATING EXISTING ADAPTIVE INTRAOCULAR LENSES

(71) Applicants: Avi Hadad, Ashkelon (IL); Edward Averbukh, Jerusalem (IL); Yoel Arieli, Jerusalem (IL)

(72) Inventors: Avi Hadad, Ashkelon (IL); Edward Averbukh, Jerusalem (IL); Yoel Arieli, Jerusalem (IL)

( * ) Notice: Subject to any disclaimer, the term of this patent is extended or adjusted under 35 U.S.C. 154(b) by 33 days.

(21) Appl. No.: 15/577,645

(22) PCT Filed: May 25, 2016

(86) PCT No.: PCT/IL2016/050541
§ 371 (c)(1),
(2) Date: Nov. 28, 2017

(87) PCT Pub. No.: WO2016/189530
PCT Pub. Date: Dec. 1, 2016

(65) Prior Publication Data
US 2018/0161150 A1 Jun. 14, 2018

Related U.S. Application Data

(60) Provisional application No. 62/167,440, filed on May 28, 2015.

(51) Int. Cl.
*A61F 2/16* (2006.01)

(52) U.S. Cl.
CPC .......... *A61F 2/1624* (2013.01); *A61F 2/1618* (2013.01); *A61F 2/1635* (2013.01); *A61F 2/1629* (2013.01); *A61F 2002/1682* (2015.04); *A61F 2002/16905* (2015.04); *A61F 2002/16965* (2015.04); *A61F 2210/0085* (2013.01)

(58) Field of Classification Search
None
See application file for complete search history.

(56) References Cited

U.S. PATENT DOCUMENTS

| | | | |
|---|---|---|---|
| 4,888,012 A | * | 12/1989 | Horn ............. A61F 2/1613 623/6.13 |
| 2007/0088433 A1 | | 4/2007 | Esch et al. |
| 2014/0180405 A1 | | 6/2014 | Weinschenk, III et al. |
| 2014/0180406 A1 | | 6/2014 | Simpson |
| 2014/0228949 A1 | | 8/2014 | Argento et al. |

FOREIGN PATENT DOCUMENTS

| | | |
|---|---|---|
| WO | 2011137191 A1 | 11/2011 |
| WO | 2013038309 A1 | 3/2013 |
| WO | 2014152017 A1 | 9/2014 |

OTHER PUBLICATIONS

Segal, Liviu, Authorized Officer, Israel Patent Office, "International Search Report" in connection with related International Application No. PCT/IL2016/050541, dated Sep. 25, 2016, 4 pages.
European Patent Office, "Extended European Search Report" in connection with related European Patent Application No. 16799475.5, dated Jan. 11, 2019, 9 pages.

* cited by examiner

*Primary Examiner* — Leslie Lopez
(74) *Attorney, Agent, or Firm* — Kolisch Hartwell, P.C.

(57) ABSTRACT

An adjustable optical power intraocular lens includes a flexible lens, flexible haptics and flexible cushions. At least one of these elements is made of a UV sensitive material that can be made rigid by UV radiation.

12 Claims, 5 Drawing Sheets

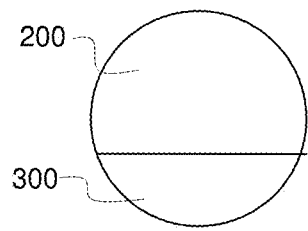
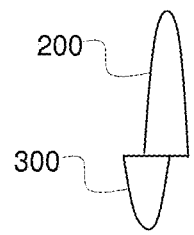
FIG. 9a  FIG. 9b
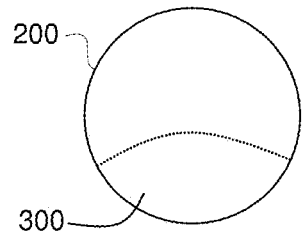
FIG. 10

INTRAOCULAR LENS AND METHODS FOR ACCOMMODATING EXISTING ADAPTIVE INTRAOCULAR LENSES

FIELD OF THE INVENTION

The present invention relates to multifocal intraocular lens. More specifically, the present invention relates to an eyelid controlled zonal multifocal intraocular lens and methods to accommodate existing intraocular lens.

BACKGROUND OF THE INVENTION

An intraocular lens (IOL) is a device that is able to simulate the ability of the natural lens of a young individual to focus at different distances effortlessly. This ability usually diminishes with age culminating in presbyopia (inability to focus at near) around the age of 45 to 50. There are several reasons for this phenomenon, the rigidity of the aging lens being the main.

The artificial intraocular lenses available today are monofocal lenses or multifocal by design. These lenses, while flexible during insertion, are not intended to move or to focus inside the eye. The multifocal lenses have two or more focal distances and the amount of focused light is necessarily reduced, because part of the lens is focused for distance and another part is focused for near. That means that part of the lens is always not focusing the image properly. That also means that multifocal lenses create visual aberrations due to dispersed light coming from the part of the lens that is not focusing properly.

Accommodative intraocular lens is an artificial lens in which its optical part needs to be flexible to be able to change focus. The obvious solution for that is a lens that is at least partially liquid.

The accommodative intraocular lens should be mechanically coupled to the contracting ciliary muscle that is in charge of accommodation. This muscle is located circumferentially behind the iris and its contraction normally pulls the zonular fibers that are normally attached to the lens capsule. However, weakening of the zonular fibers may contribute to the lack of focusing. Thus part of the accommodative lens haptics should be in direct contact with the ciliary muscle, pressing against it. That means that the lens should be located in the ciliary sulcus, between the natural lens capsule and the iris.

Since the size of the eye varies, a flexible lens allows the haptics to open in a spring-like fashion where the haptics rest on the diametrically opposing sides of the ciliary muscle and the optic is centered in front of the pupil. It also allows insertion of the lens through a small cut.

However the same flexibility will prevent the transmission of forces from the ciliary muscle to the optical part. The flexible haptics will absorb whatever contracting forces of the ciliary muscle exerts, preventing any significant force to reach the optical part of the lens.

SUMMARY OF THE INVENTION

It is therefore an object of the present invention to provide a method and apparatus that provide reduced amount of unfocused light and a method and an apparatus that reduce the absorption of the contracting forces that the ciliary muscle exerts.

According to one embodiment of the present invention the flexible parts of the lens haptics are made at least partially from a material that can change its properties and become rigid.

According to another embodiment of the present invention the flexible parts of the lens haptics are made of a polymer that becomes rigid after exposure to ultraviolet light. The haptics and the joints between the haptics and the IOL are the parts that become rigid by curing them after of the surgical implantation.

According to another embodiment of the present invention different flexible parts of the lens are made of a UV-sensitive material which are cured after of the surgical implantation.

According to another embodiment of the present invention the internal liquid pressure of a liquid lens is accommodated by puncturing bubbles located in the liquid lens and thus accommodating its optical power.

According to another embodiment of the present invention the multifocal IOL comprises of several not-circular symmetric regions with different focal lengths and different relative areas, where the proportions of the relative areas of the different regions where light is propagating through, are controlled by the eyelids.

BRIEF DESCRIPTION OF THE DRAWINGS

In order to understand the invention and to see how it may be carried out in practice, embodiments will now be described, by a way of non-limiting examples only, with reference to the accompanying drawing, in which:

FIG. 9a shows a front view of another embodiment of a multifocal IOL according to the present invention.

FIG. 9b shows a cross section view of another embodiment of a multifocal IOL according to the present invention.

FIG. 10 shows a front view of another embodiment of a multifocal IOL according to the present invention.

DETAILED DESCRIPTION OF INVENTION

Figure 1A:
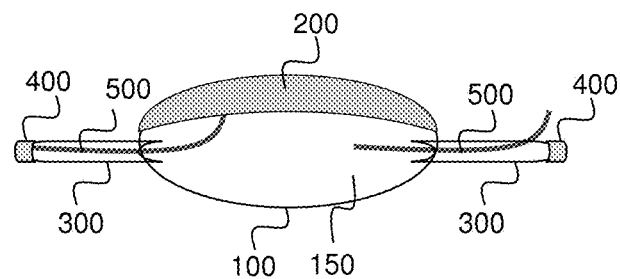
FIG. 1a describes the side view of a first embodiment of an intraocular lens (IOL) according the present invention.
Figure 1B:
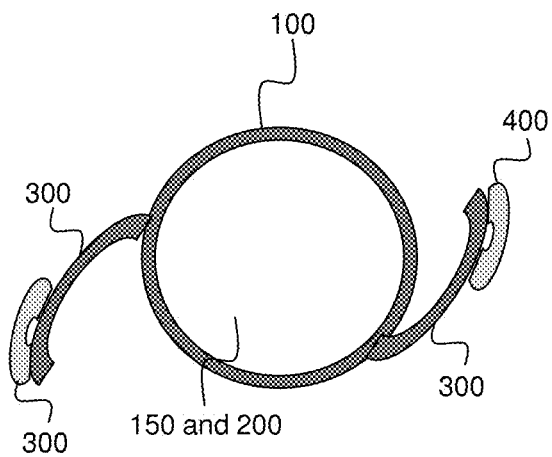
FIG. 1b describes the top view of the first embodiment of an IOL according the present invention.

FIGS. 1a and 1b show the side view and the top view, respectively, of one embodiment of a flexible intraocular lens (IOL) according to the present invention. This embodiment is only for the purpose of illustrating the main idea of the present invention. In this embodiment, the IOL 100 comprises a flexible lens 150 which may be of zero optical power for add-on sulcus lens or any other optical power, a liquid lens 200 in which its curvature may by modified by the liquid pressure and thus the overall optical power of the IOL 100, haptics 300 which are made of a UV sensitive material that is initially flexible but may be turned into rigid by UV radiation, flexible cushions filled of liquid 400 which are resting on the ciliary body and communicating with the liquid lens through a pipe 500 that joins the liquid of the flexible cushions and the liquid of the liquid lens. The overall optical power composes the optical power of the lens 150 and the optical power of the liquid lens 200. The inner surface of the liquid lens 200 may or may not be in contact with the inner surface of the lens 150. When the liquid pressure of the liquid lens changes, the curvature of the outer surface of the liquid lens is changed too, and thus its optical power is modified. The liquid pressure of the liquid lens may depend on multiple factors inside the eye. The most important factor is the haptics pressure on the ciliary body that will result in deformation of liquid cushions and change the liquid pressure. When the ciliary muscle changes its contraction, the pressure on the ciliary body will be changed and this results in changes of the deformation of the liquid cushions and thus the liquid pressure. Since the liquid of the cushions 400 is communicating with the liquid of the liquid lens, the changes of the liquid pressure modifies the outer surface of the liquid lens and thus its optical power. However since the haptics are initially flexible, this flexibility will prevent the complete transmission of forces from the ciliary muscle to the optical part. To stop this from happening the flexible parts of the lens haptics are made, at least partially, from a material that can change its physical properties and become rigid. This material may be for example, a polymer that becomes rigid after exposure to ultraviolet light or a material that becomes rigid after exposure to higher temperature. Thus, the haptics and the joints between the haptics and the IOL 100 may become rigid by curing them. After the surgery, when the IOL is located in its place, a UV or IR radiation is directed to the flexible haptics and the joints between the haptics and the liquid lens and turns them into rigid.

Figure 2:
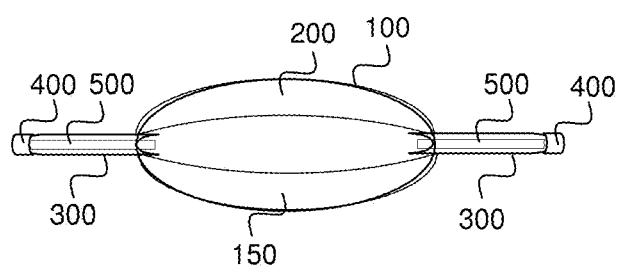
FIG. 2 describes another embodiment of a flexible IOL according the present invention.

FIG. 2 shows a side view of another embodiment of a flexible intraocular lens (IOL) according to the present invention. In this embodiment, the IOL 100 comprises a first lens 150 made of flexible UV sensitive material which may be of zero power for add-on sulcus lens or any other power and a second lens 200 also made of flexible UV sensitive material. There is a space between both lenses 150 and 200 filled of liquid or some other material that can deliver the forces from the ciliary mussels. The IOL also comprises haptics 300 which also are made of a UV sensitive material, flexible cushions filled of liquid 400 which are resting on the ciliary body and communicating with the liquid lens through a pipe 500 that joins the liquid of the flexible cushions and the liquid between the lenses 150 and 200. After the surgery, UV or IR illumination is directed to the lenses 100 and 200, the haptics 300 and the joints between the haptics and the IOL 100 and transform them into rigid. Thus, when the ciliary muscle changes its contraction, the pressure on the ciliary body will be changed and this results in changes of the deformation of the liquid cushions and the liquid pressure. Since the liquid of the cushions 400 is connected to liquid in the space between the two lenses 100 and 200, the changes of the liquid pressure modifies the distance between both lenses and thus the optical power of the IOL changes.

It may be emphasized that the embodiments described above are only for illustration and the main idea of the present invention is to describe a method for turning parts of a flexible IOL into rigid after the surgery, thus, on one hand, before the surgery the IOL is flexible and may allow its insertion through a small cut, but after the surgery, parts of the IOL are turned into rigid inside the eye to create an accommodating IOL with higher efficiency.

It is also noted that the material that deliver the forces from the ciliary mussels to change the distances or/and the structure of any of the optical parts of the IOL to modify its optical power may also be any material such as gas, gel or solid.

It is also noted that the material that forms the parts of the IOL that are transformed from flexible to rigid may be any material that can be transformed from flexible into rigid by any physical or chemical process or any combination of them.

The said parts of the IOL to be transformed from flexible to rigid may be any part or parts of the IOL or any combination of them.

Figure 3:
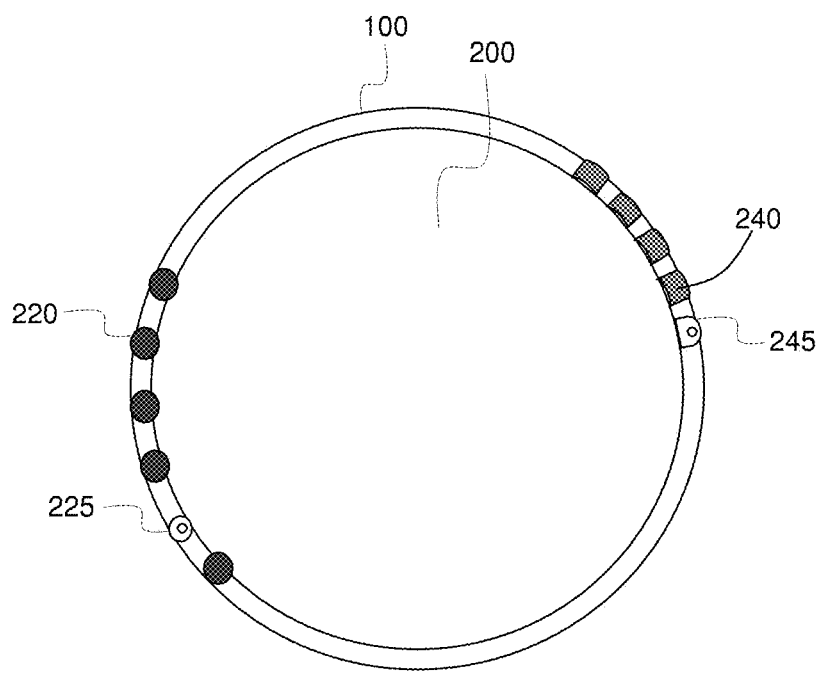
FIG. 3 shows a top view of an embodiment of an IOL according to the present invention wherein the liquid pressure inside the lens can be adjusted.

FIG. 3 shows a top view of an embodiment of an intraocular lens (IOL) according to the present invention wherein the liquid pressure inside the lens can be adjusted. This embodiment may be similar to the previous embodiment which includes a liquid lens 200, except for additional multiple bubbles 220 and 240 that are added at the circumference of the liquid lens 200. The liquid pressure may depend on multiple factors inside the eye where the most important of these is the haptics pressure on the ciliary body that will result in deformation of liquid cushions as described in the previous embodiment. However, the final factors that determine the liquid pressure inside the lens are difficult to predict before surgery, so the final curvature of the liquid lens inside the eye is also difficult to predict. Some adjustment mechanism is needed. We suggest the following adjustment mechanism. Multiple bubbles made of semi-rigid material will be placed at the circumference of the liquid lens. These bubbles will share a flexible wall with the liquid lens. Some of these bubbles (220) will be initially inflated to have a high liquid pressure thus resulting in some bulging of the shared wall into the liquid lens space. The bubbles will be filled with a liquid that is bio-compatible with the aqueous humor. Puncturing such a bubble (such as shown in 225) with YAG laser or a mechanically will reduce its internal pressure thus the flexible shared wall will stop bulging into the lens. This will effectively reduce the internal liquid pressure inside the lens. Puncturing several of such bubbles will allow to reduce the curvature of the liquid lens in a step-wise manner. Some other similar bubbles (240) may be fashioned to have low pressure (vacuum) resulting in outward bulging of the shared wall of the liquid lens. Puncturing a low-pressure bubble (such as shown in 245) will result in elevation of the pressure inside the liquid lens, thus increasing its curvature and the optical power. After proper adjustment and stabilization of the lens, the lens may be cured to become rigid, no longer flexible except for the central optics, by irradiating it with UV or IR light.

Alternatively, at least one flexible cushion or a flexible tire filled with liquid may be added at the circumference of the liquid lens 200. The adjustment of the liquid pressure at the liquid lens may be controlled by filling the flexible cushion or the tire with more liquid or draining it in a step-wise manner. After proper adjustment and stabilization of the lens, parts of the lens may be cured to become rigid by irradiating it with UV or IR light.

It is emphasized here that the embodiment described here is only for illustration to describe a method for adjusting the liquid pressure inside an accommodating IOL that includes liquid inside, after surgery. Accordingly, the IOL may be any kind of known IOLs that includes liquid inside. The said adjusting of the liquid pressure with said bubbles or said flexible tire may control surface curvatures of optical elements which are parts of the IOL, distances between different parts of the IOL that may be varied according the liquid pressure inside the IOL or any other physical parameters that may be varied according the liquid pressure inside the IOL.

Figure 4A:
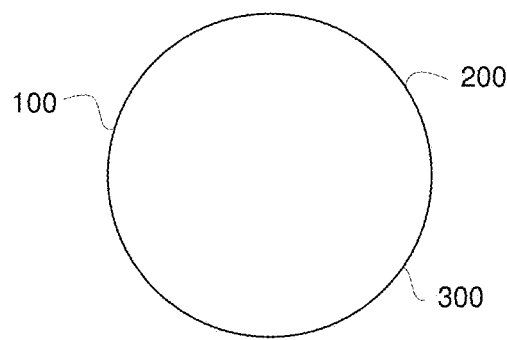
FIG. 4a shows a front view of a multifocal IOL according to the present invention.
Figure 4B:
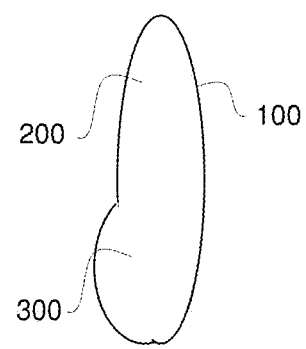
FIG. 4b shows a cross section view of a multifocal IOL according to the present invention.
Figure 5A:
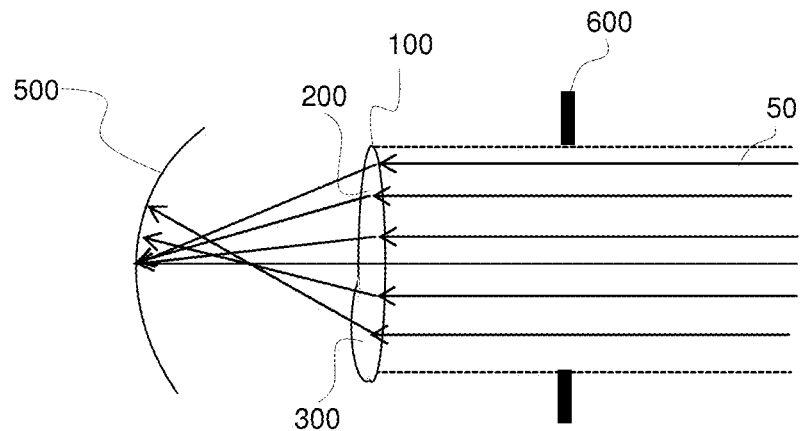
FIG. 5a shows the rays of light when the eyelid is open.
Figure 5B:
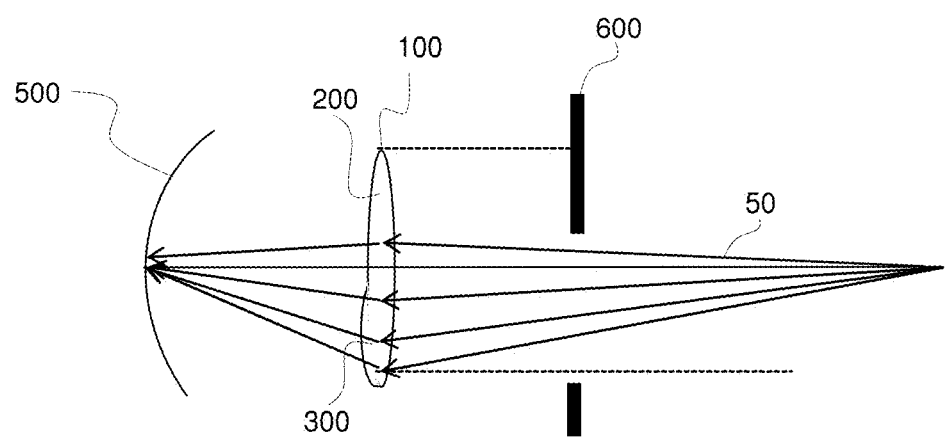
FIG. 5b shows the rays of light when the eyelid is half closed.

FIGS. 4a and 4b show a front and a cross section views of a multifocal intraocular lens (IOL) according to the present invention. The IOL 100 is divided to at least two different regions 200 and 300 with different focal lengths and different areas. The IOL is divided to non-circular symmetric regions but from up to down. When the light from any point of the scene penetrates through the eye pupil it propagates through the IOL 100. However, since the IOL has different regions with different focal lengths the light rays from any point of the scene are focused at different planes, which only one of them may coincide with the retina. The light rays that are not focused on the retina may cause a blurred image of that point. In order to reduce the effect of the not focused light it suggested here to divide the IOL 100 to at least two different regions with non-equal areas such that the proportions of the areas of the various regions are controlled by the position of the eyelids. In this scheme, according to the position of the eyelid the proportions of the areas of the various regions are varied and the largest amount of light penetrates to the eye at the region with the largest area, and thus the dominant focal length is the focal length with the largest area. An illustration is shown schematically in FIGS. 5a and 5b. In this illustration, the IOL 100 has two regions 200 and 300, where the upper region 200 has longer focal length and larger area and the lower region 300 has shorter focal length and smaller area. When the eyelid 600 is open as shown in FIG. 5a, most of the light rays 50 penetrate to the eye through region 200 with the longer focal length. If the patient is looking at a distant object most of the rays are focused on the retina 500 and the effect of blurring due the non-focused light from the lower region 300 is small. On the other hand, when the eyelid is half closed as shown in FIG. 5b, the largest area now is region 300 which has the shortest focal length. If the patient is looking at a close object most of the rays are focused on the retina 500 and the effect of blurring due the non-focused light from the upper region 200 is small.

It may be noted that the embodiment described above are only for illustration and the opposite situation where the upper region 200 has shorter focal length and larger area and the lower region 300 has longer focal length and smaller area or the opposite can also be applied. Intermediate focal lengths may also be applied.

Figure 6A:
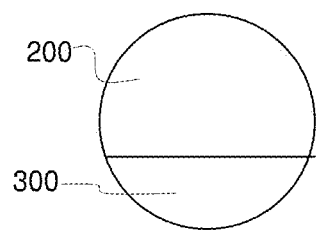
FIG. 6a shows a front view of another embodiment of a multifocal intraocular lens (IOL) according to the present invention.
Figure 6B:
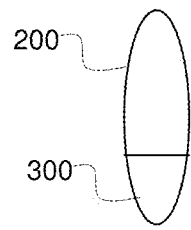
FIG. 6b shows a cross section view of another embodiment of a multifocal IOL according to the present invention.

The different focal lengths of the different regions can be obtained by several methods and/or their combinations:

FIGS. 6a and 6b show schematically a side and a front view of one embodiment of a multifocal IOL 100 with two regions with different focal lengths due to different refractive indices. The two regions have different areas as described above. In this illustration, region 200 has long focal length due to one refractive index and region 300 has short length due to a different refractive index. The process of how it works is similar to what described above.

Figure 7A:
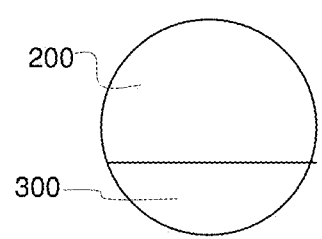
FIG. 7a shows a front view of another embodiment of a multifocal IOL according to the present invention.
Figure 7B:
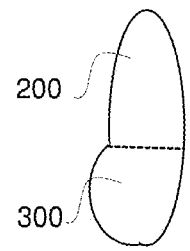
FIG. 7b shows a cross section view of another embodiment of a multifocal IOL according to the present invention.

FIGS. 7a and 7b show schematically a side and a front view of another embodiment of a multifocal IOL 100 with two regions with different focal lengths due to surface's curvatures. The two regions have different areas as described above. In this illustration, region 200 has long focal length due to one surface's curvatures and region 300 has short length due to a different surface's curvatures. The process of how it works is similar to what described above.

Figure 8A:
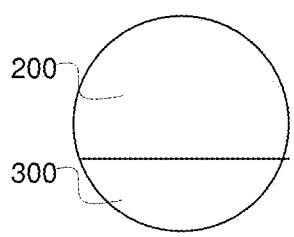
FIG. 8a shows a front view of another embodiment of a multifocal IOL according to the present invention.
Figure 8B:
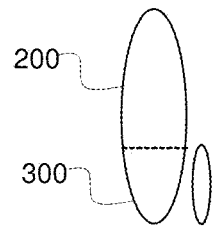
FIG. 8b shows a cross section view of another embodiment of a multifocal IOL according to the present invention.

FIGS. 8a and 8b show schematically a side and a front view of another embodiment of a multifocal IOL 100 with two regions with different focal lengths due to combination of several optical elements with different optical powers. The two regions have different areas as described above. In this illustration, region 200 has long focal length due to one combination of several optical elements with different optical powers and region 300 has short length due to a different combination of several optical elements with different optical powers. The process of how it works is similar to what described above.

FIGS. 9a and 9b show schematically a side and a front view of another embodiment of a multifocal IOL 100 with two regions with different areas as described above. In this illustration, both regions have the same optical power but they are located in different distances relative to the retina, one region is far from the retina and one region is close to the retina. Thus, the two parts of the lens focus the rays coming from distant or close object's points at different locations. Rays from distant object's point that penetrate trough the region with the longer distance from the retina are focused on the retina but those that penetrate trough the region with the shorter distance from the retina are focused previous to the retina. Rays from close object's point that penetrate trough the region with the longer distance from the retina are focused behind the retina but those that penetrate trough the region with the shorter distance from the retina are focused on the retina. If the patient is looking at a distant object most of the rays are focused on the retina and the effect of blurring due the non-focused light from the lower region is small. On the other hand, when the eyelid is half closed, the largest area now is the lower region which is closer to the retina and if the patient is looking at a close object most of the rays are focused on the retina and the effect of blurring due the non-focused light from the upper region is small.

The above embodiments are only for illustration and some parts of the IOL such as the haptics etc. are omitted in order to illustrate the idea. In real IOL, these parts may be added.

The different areas of the IOL may also be separated by any curved line as shown schematically in front view in FIG. 10, provided that the eyelid movement controls the relative effective area of the lens such that in different eyelid positions the dominant desired focus will changed accordingly.

According to the present invention, the optical system of the IOL is a bistable system, that is, it is stable only in discrete states and it is not stable in all continues states. In the different stable discrete states the IOL has different focal lengths. Several examples are described in the following where the focal length is controlled by the gravity and the position of the head:

a) In one position of the head, the gravity causes a curving of a membrane (like trampoline) where in both sides of the membrane there are lenses, one is fixed and one is moveable with the membrane.

b) In one position of the head (down), the gravity causes an additional optical element to move and to be placed in the optical axis. In the other position (head up) the gravity causes the additional optical element to move from the optical axis (like doll's eyes that are open or closed according to its position).
c) In one position of the head, the gravity causes a fluid with a different refractive index to be positioned in the optical axis (head down). In the other position (head up) the gravity causes the additional the fluid with a different refractive index to be positioned in the optical axis—according to the communicating vessels law.
d) In one position of the head, the gravity causes a fluid to push an air bubble to be positioned in the optical axis (head down) between two lenses. In the other position (head up) the gravity causes the fluid to push the air bubble out of the optical axis. This causes two effects: 1. A refractive index change in the space between the two lenses. 2. Changes the relative positions of the two lenses.
e) In one position of the head, the gravity causes a fluid to push an air bubble to be positioned in the optical axis (head down) between two lenses. In the other position (head up) the gravity causes the fluid to push the air bubble out of the optical axis. This causes two effects: 1. A refractive index change in space between the two lenses. 2. Changes the relative positions of the two lenses.

According to the present invention, the focal length of the IOL is controlled by magneto-wetting. A transparent fluid with magnetowetting characteristics is place on a transparent material. The fluid changes its surface's curvature due its wetting characteristics and the surface tension in corresponding to the material is placed on, due to a magnetic field that is applied. The magnetic field can be changed and controlled by the eyelids or the eyelashes positions whereby a magnetic powder is sprinkled on, or by an auxiliary device.

According to the present invention, the focal length of the IOL is controlled by a smartphone where inside the IOL there is an electronic device and/or a mechanical system. The distances and/or the surface's curvatures of the optical elements in the IOL, are controlled by a smartphone or some other remote system

What is claimed is:

1. An apparatus comprising:
   an adjustable-optical-power intraocular lens comprising:
   at least one flexible lens that comprises a liquid;
   flexible haptics which are attached to said at least one flexible lens;
   a plurality of bubbles comprising a semi-rigid material disposed around the circumference of the liquid lens; and
   a flexible wall disposed between the bubbles and the lens that comprises the liquid,
   wherein the bubbles are configured to be punctured, such as to adjust pressure of the liquid of the flexible lens.

2. The apparatus according to claim 1, wherein the liquid of the lens that comprises the liquid is a first liquid, and wherein the intraocular lens further comprises flexible cushions that are attached to said haptics and that are filled with a second liquid.

3. The apparatus according to claim 2, wherein the intraocular lens further comprises pipes which communicate between the second liquid in said cushions and the first liquid of the lens.

4. The apparatus according to claim 3, wherein the pipes are made of a UV sensitive material.

5. The apparatus according to claim 1, wherein:
   the intraocular lens further comprises two further flexible lenses that define a space therebetween, and
   said flexible lens that comprises the liquid fills the space between the two further flexible lenses.

6. The apparatus according to claim 1, wherein the flexible haptics are configured to be turned rigid by UV radiation.

7. The apparatus according to claim 1, wherein the bubbles comprise bubbles that are initially inflated to have a lower liquid pressure than that of the flexible lens, such that the flexible wall disposed between the bubbles and the liquid lens bulges into the bubbles, and wherein the bubbles are configured such that puncturing the bubbles increases the pressure of the liquid inside of the flexible lens.

8. An adjustable-optical-power intraocular lens comprising:
   at least one flexible lens having an outer flexible wall defining an inner space that contains a liquid, and
   a plurality of bubbles formed in said flexible wall and formed of a semi-rigid material that can be punctured, so as to adjust pressure of the liquid of the flexible lens;
   wherein at least some of the bubbles are initially inflated to have a higher liquid pressure than that of the flexible lens, such that the bubbles bulge into the flexible wall of the liquid lens, and the bubbles are configured such that puncturing the bubbles reduces the pressure of the liquid inside of the flexible lens.

9. The adjustable-optical-power intraocular lens according to claim 8, wherein the flexible lens has zero optical power at rest.

10. The adjustable-optical-power intraocular lens according to claim 8, further including flexible haptics that are attached to the flexible lens and are configured to be turned rigid by UV radiation.

11. The adjustable-optical-power intraocular lens according to claim 8, wherein the bubbles are configured to be punctured using a YAG laser.

12. The adjustable-optical-power intraocular lens according to claim 8, wherein the bubbles are configured to be punctured mechanically.

* * * * *